United States Patent [19]

Bommer et al.

[11] Patent Number: 5,066,274

[45] Date of Patent: * Nov. 19, 1991

[54] TETRAPYRROLE THERAPEUTIC AGENTS

[75] Inventors: Jerry C. Bommer, Ogden; Bruce F. Burnham, Logan, both of Utah

[73] Assignee: Nippon Petrochemicals Company, Ltd., Tokyo, Japan

[ * ] Notice: The portion of the term of this patent subsequent to Sep. 15, 2004 has been disclaimed.

[21] Appl. No.: 351,770

[22] Filed: May 12, 1989

Related U.S. Application Data

[63] Continuation-in-part of Ser. No. 728,786, Apr. 30, 1985, abandoned.

[51] Int. Cl.$^5$ .............................................. A61N 1/30
[52] U.S. Cl. ......................................... 604/20; 424/2; 540/145; 514/410
[58] Field of Search ............... 604/20, 49; 260/245.91; 424/9, 2; 540/145; 514/410, 322

[56] References Cited

U.S. PATENT DOCUMENTS

| | | | |
|---|---|---|---|
| 4,104,466 | 8/1978 | Tsuchida et al. | 260/245.91 |
| 4,393,071 | 7/1983 | Fujii et al. | |
| 4,541,438 | 9/1985 | Parker et al. | 424/9 |
| 4,634,557 | 1/1987 | Sato | 424/9 |
| 4,649,151 | 3/1987 | Dougherty et al. | 540/145 |
| 4,656,186 | 4/1987 | Bommer et al. | 514/322 |
| 4,675,338 | 6/1987 | Bommer et al. | 514/410 |
| 4,693,885 | 9/1987 | Bommer et al. | 514/410 |

FOREIGN PATENT DOCUMENTS

| | | |
|---|---|---|
| 0071991 | 2/1983 | European Pat. Off. . |
| 0168832 | 1/1986 | European Pat. Off. . |
| 0186962 | 7/1986 | European Pat. Off. . |
| 2809093 | 3/1977 | Fed. Rep. of Germany ...... 514/410 |
| 834574 | 7/1960 | France ............................... 514/410 |
| 2850676 | 3/1976 | Japan . |
| 0201793 | 1/1983 | Japan ............................. 260/245.91 |
| 8300811 | 3/1983 | PCT Int'l Appl. . |
| 8401382 | 4/1984 | PCT Int'l Appl. . |

OTHER PUBLICATIONS

Clezy et al. "The Chemistry of Pyrrolic Compounds. XXXIX Dihydro and Monohydrated Derivatives of Protoporphyrin IX", *Aust. J. Chem.*, 1978, vol. 31, pp. 365-379.
Lautsch et al., *Chem. Ber.* 90(4): 470–481, (1957).
Losse & Muller, *Hoppe-Seyler's Ztschr. Phys. Chem.*, 327, 205–216, (1962).
Karrer, *Chimia*, 13, 129–180 (1959).
Pelter et al., *Tetrahedron Letters*, 23, 2017–2020 (1978).
Gauthier et al., *Current Microbiology*, 8, 195–199 (1983).
Bancunbee et al., *Zhurnal Organicheskoi Kii Mii*, 15, 815–835 (1979).
Lin et al., *Porphyrin Localization and Treatment of Tumors*, 187–199 (1984) edited by Doiron and Gomer, Alan R. Liss, NY, NY.
Benson, *Porphyrin Localization and Treatment of Tumors*, 795–804 (1984) edited by Doiron and Gomer, Alan R. Liss, Inc. New York, NY.
Doiron et al., *Porphyrins in Tumor Phototherapy*, 395–403 (1984) edited by Andreoni and Cubeddu, Plenum Press, New York, NY.
Spinelli, *Porphyrins in Tumor Phototherapy*, 423–426 (1984) edited by Andreoni and Cubeddu, Plenum Press, New York, NY.
Ohi et al., *Porphyrins in Tumor Phototherapy*, 439–446 (1984) edited by Andreoni and Cubeddu, Plenum Press, New York, NY.
Bruce, *Porphyrins in Tumor Phototherapy*, 455–461 (1984) edited by Andreoni and Cubeddu, Plenum Press, New York, NY.
Aizawa et al., *Porphyrin Localization and Treatment of Tumors*, 227–238 (1984) edited by Doiron and Gomer, Alan R. Liss, Inc. NY, NY.
Grenan et al., *Research Communications and Chemical Pathology and Pharmacology*, 30, 317–327 (1980).
*Chemical Abstracts* 89: 157470p (1978).
*Chemical Abstracts* vol. 83, 172597e (1975).
*Chemical Abstracts*, vol. 84, 38612y (1976).
*Chemical Abstracts*, vol. 89, 12383y (1978).
*Chemical Abstracts* 90: 16079b (1978).
*Chemical Abstracts* 90, 16078a (1978).
Kessel et al., *Photochemistry and Photobiology* 40, 403–406 (1984).
Dougherty et al., *Journal of the National Cancer Institute*, 55, 1976, pp. 115–119.
Wile et al., "Laser Photoradiation Therapy of Recurrent Human Breast Cancer and Cancer of the Head and Neck," in *Porphyrin Photosensitization*, ed. by Kesser and Dougherty, Alan R. Liss, Inc., New York, NY, pp. 47–52 (1973).
Henderson et al., "Studies on the Mechanism of Tumor Destruction by Photoradiation Therapy," in *Porphyrin Localization and Treatment of Tumors*, ed. by Dorion and Gomer, Alan R. Liss, Inc., New York, NY, pp. 601–612 (1984).
Hayata et al., "Indications of Photoradiation Therapy in Early Stage Lung Cancer on the Basis of Post-PRT Histologic Findings," in *Porphyrin Localization and Treatment of Tumors*, ed. by Dorion and Gomer, Alan R. Liss, Inc., New York, NY, pp. 747–758 (1984).
Profio et al., "Fluorescence of Hematoporphyrin-Derivative for Detection and Characterization of Tumors," in *Porphyrins in Tumor Photo-therapy*, ed. by Andreoni and Cubeddu, Plenum Press, New York, NY, pp. 321–337 (1984).
Fioretti et al., "Monitoring of Hematoporphyrin Injected in Humans and Clinical Prospects of Its Use in Gynecologic Oncology," in *Porphyrins in Tumor Phototherapy*, ed. by Andreoni and Cubeddu, Plenum Press, New York, NY, pp. 355–361 (1984).

*Primary Examiner*—Stephen C. Pellegrino
*Assistant Examiner*—Michael Rafa
*Attorney, Agent, or Firm*—Scully, Scott, Murphy & Presser

[57] ABSTRACT

This invention relates to a therapeutic composition for detection and/or treatment of mammalian tumors which comprises at least one fluorescent porphyrin containing at least three carboxylic acid groups and pharmaceutically acceptable salts thereof.

35 Claims, No Drawings

TETRAPYRROLE THERAPEUTIC AGENTS

BACKGROUND OF THE INVENTION

This is a continuation in part of copending U.S. patent application Ser. No. 728,786, which was filed on Apr. 30, 1985, now abandoned.

FIELD OF THE INVENTION

This invention relates to new therapeutic compositions which are useful in photodiagnosis and phototherapy, especially in the detection and treatment of tumors and cancerous tissues in the human or animal body.

DESCRIPTION OF THE PRIOR ART

It is known to irradiate tumors and cancerous tissues in the human body with intensive light following administration of a hematoprophyrin derivative in the wavelength range of 626 to 636 nanometers to reduce and, at times, destroy the cancerous cells (see PCT published specification WO83/00811). It is also known that porphyrins, especially the sodium salt of protoporphyrins, can maintain or promote the normal functions of cells and are useful for preventing the genesis, growth, metastasis, and relapse of malignant tumors. Japanese Published Patent Application No. 125737/76 describes the use of porphyrins as tumor inhibiting agents, exemplifying etioporphyrin, mesoporphyrin, protoporphyrin, deuteroporphyrin, hematoporphyrin, coproporphyrin, and uroporphyrin.

That some of the tetrapyrroles cause intense photosensitivity in animals is well-known and has been documented in numerous articles in literature, e.g., J. Intr. Sci. Vitaminol, 27, 521–527 (1981); Agric. Biol. Chem., 46(9), 2183–2193 (1982); Chem. Abst. 98, 276 (1983) and 88, 69764 m (1928).

SUMMARY OF THE INVENTION

The present invention is directed to a pharmaceutical composition for the detection of mammalian tumors which comprises a tumor-detecting effective amount of a light sensitive tetrapyrrole compound of formula I

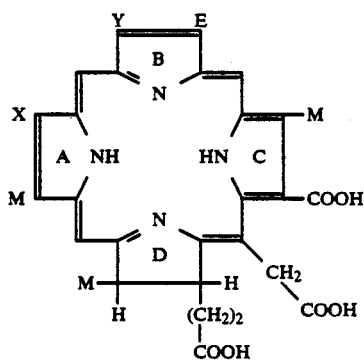

or pharmaceutically acceptable salts thereof wherein

X = H, vinyl, ethyl, acetyl or formyl;

Y = methyl, formyl or ( H, methyl )

E = ethyl or ( H, ethyl ) and

M = methyl

M = methyl and a pharmaceutical carrier therefor, wherein said compound is capable of being activated by light of sufficient wavelength to emit fluorescence thereof.

The compounds of the present composition are used for detecting tumors in a mammal by administering to said mammal a tumor detecting effective amount of said compounds, applying light of sufficient wavelength to the area of the mammal to be examined, said wavelength being in the range of about 360 nm to about 760 nm, and observing the emitted fluorescence from the compound located at said tumor. Accordingly, the present invention is also directed to the method of using said compounds for detecting tumors.

The present invention is also directed to a pharmaceutial composition for the treatment of tumors which comprises an anti-tumor effective amount of a light-sensitive tetrapyrrole compound of the formula

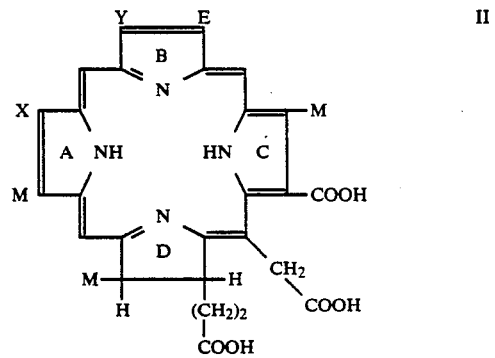

or pharmaceutically acceptable salts thereof wherein

X = H, vinyl, ethyl, acetyl or formyl;

Y = methyl, formyl or ( H, methyl )

M = methyl; and

E = ethyl or ( H, ethyl )

and a pharmaceutical carrier therefor, wherein said compound is capable of being activated by light of sufficient wavelength to exert a cell-killing effect on said tumor, with the proviso that said compound is not chlorin e$_6$.

These latter compounds of the present composition can be used to treat tumors in a mammal by administering to said mammal an anti-tumor effective amount of these compounds, applying light of sufficient wavelength and intensity to activate said compound, said wavelength being in the range from about 600 to about 800 nm. These activated compounds exert a cell-killing effect on said tumor. Accordingly, the present invention is also directed to the method of using these compounds for treating tumors.

DETAILED DESCRIPTION OF THE INVENTION

The therapeutic agents of the present invention are tetrapyrrole carboxylic acids which are known per se or preparable by various procedures from naturally-occurring tetrapyrroles. The sole characteristic of the present therapeutic agents is the presence of at least three carboxylic acid groups in the molecule.

The cyclic tetrapyrroles have as their common parent tetrapyrrole, uroporphyrinogen, and possess the following ring structure:

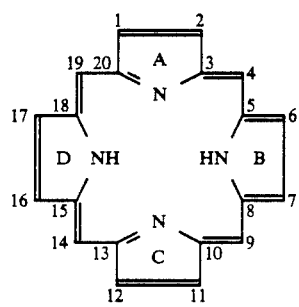

in which the positions in the molecule are numbered 1-20, and the rings identified by letters A, B, C and D, and also include perhydro-, e.g., dihydro- and tetrahydro-, derivatives of the said ring structure, e.g., compounds in which one or more double bonds are absent. There are present in the ring system four pyrrole rings joined through the alpha positions of the respective pyrrole rings by a methine group, i.e., —CH=. The active compounds in the compositions of the present invention are designated as derivatives of the tetrapyrroles for convenience in the disclosure and the appended claims and it will be understood that the term "tetrapyrrole" will designate compounds of the characteristic ring structure designated hereinbefore as well as the corresponding perhydro derivatives.

The tetrapyrroles employed in the present invention are all known or derived by various means and various alteration procedures from natural tetrapyrroles. The naturally occurring tetrapyrroles have as their common ancestor uroporphyrinogen III, a hexahydroporphyrin reduced at the bridge positions. The preferred tetrapyrrole carboxylic acids are those wherein at least three carboxylic acid groups are present in the tetrapyrrole, preferably asymmetrically attached to the porphyrin ring system, e.g., the carboxylic acid groups are present on the rings A and B side of the molecule or on the rings D and C side of the molecule.

The particularly preferred compositions use compounds described by the formula:

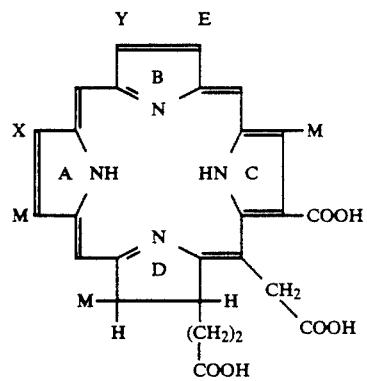

or pharmaceutically acceptable salts thereof wherein, X, Y, M and E are defined hereinabove. More specifically, when used for the detection of tumors, the variables have the following definitions:

X = H, vinyl, ethyl, acetyl or formyl;

Y = methyl, formyl or $\begin{cases} H \\ methyl; \end{cases}$

M = methyl; and

E = ethyl or $\begin{cases} H \\ ethyl. \end{cases}$

On the other hand, when used for the treatment of tumors, the X, Y, M and E are as defined above with the proviso that the compound is not chlorin $e_6$.

An embodiment of the composition of the present invention used for the treatment of tumors use rhodin $g_7$ or a compound of Formula I wherein X = H, ethyl, acetyl or formyl
Y = methyl or formyl
M = methyl and;
E = ethyl Exemplary compounds used in the compositions of the tetrapyrrole classes are illustrated in Table I in which the numbered positions of the tetrapyrrole ring structure are used to designate the position of the indicated substituent. The absence of double bonds in the ring system is designated under "dihydro" with each set of numbers (ring position) indicating the absence of a double bond between the designated positions.

TABLE I

| | Ring Position | | | | | | | | | |
|---|---|---|---|---|---|---|---|---|---|---|
| | A | | B | | C | | | D | | |
| PORPHYRIN | 1 | 2 | 6 | 7 | 11 | 12 | 14 | 16 | 17 | Dihydro |
| Chlorin $e_6$ | Me | V | Me | Et | Me | $CO_2H$ | Ac | $\begin{cases} H \\ Pr \end{cases}$ | $\begin{cases} H \\ Me \end{cases}$ | 16, 17 |
| Mesochlorin $e_6$ | Me | Et | Me | Et | Me | $CO_2H$ | Ac | $\begin{cases} H \\ Pr \end{cases}$ | $\begin{cases} H \\ Me \end{cases}$ | 16, 17 |
| Bacteriochlorin a | Me | ACL | $\begin{cases} H \\ Me \end{cases}$ | $\begin{cases} H \\ Et \end{cases}$ | Me | $CO_2H$ | Ac | $\begin{cases} H \\ Pr \end{cases}$ | $\begin{cases} H \\ Me \end{cases}$ | 6, 7 16, 17 |
| 2-Desvinylchlorin $e_6$ (or Deuterochlorin $e_6$) | Me | H | Me | Et | Me | $CO_2H$ | Ac | $\begin{cases} H \\ Pr \end{cases}$ | $\begin{cases} H \\ Me \end{cases}$ | 16, 17 |
| 2-Acetylchlorin $e_6$ | Me | ACL | Me | Et | Me | $CO_2H$ | Ac | $\begin{cases} H \\ \end{cases}$ | $\begin{cases} H \\ \end{cases}$ | 16, 17 |

TABLE I-continued

| | Ring Position | | | | | | | | |
|---|---|---|---|---|---|---|---|---|---|
| | A | | B | | C | | D | | |
| PORPHYRIN | 1 | 2 | 6 | 7 | 11 | 12 | 14 | 16 | 17 | Dihydro |
| | | | | | | | | Pr | Me | |
| 2-Formylchlorin $e_6$ | Me | CHO | Me | Et | Me | $CO_2H$ | Ac | ( H / Pr | ( H \ Me | 16, 17 |
| Rhodin $g_7$ | Me | V | CHO | Et | Me | $CO_2H$ | Ac | ( H / Pr | ( H \ Me | 16, 17 |

Notes:
Me: —$CH_3$ (Methyl group)
Pr: —$CH_2CH_2COOH$ (Propionic acid group)
V: —$CH=CH_2$ (Vinyl group)
Et: —$CH_2CH_3$ (Ethyl group)
Ac: —$CH_2COOH$ (Acetic acid group)
ACL: $CH_3$—CO— (Acetyl group)

The aforesaid compounds in the present composition form salts with either acids or bases. The acid salts are particularly useful for purification and/or separation of the final products as are the salts formed with bases. The base and therapeutic use as hereindescribed.

The acid salts are formed with a variety of acids such as the mineral acids, hydrochloric, hydrobromic, nitric and sulfuric acids, and organic acids such as toluenesulfonic and benezenesulfonic acids.

The base salts include, for example, sodium, potassium, calcium, magnesium, ammonium, triethylammonium, trimethylammonium, morpholine and piperidine salts and similar such salts.

The acid and base salts are formed by the simple expediency of dissolving the selected tetrapyrrole in an aqueous solution of the acid or base and evaporation of the solution to dryness. The use of a water-miscible solvent for the tetrapyrrole can assist in dissolving the compositions.

The tetrapyrroles can also be converted to metal complexes for example by reaction with metal salts, e.g., the magnesium complexes which are useful for the same purpose as the tetrapyrrole.

PHOTODIAGNOSIS AND PHOTOTHERAPY

Compositions of the present invention are useful for the photodiagnosis and phototherapy of tumor, cancer and malignant tissue (hereinafter referred to as "tumor").

When a man or animal i.e. a mammal, having a tumor is treated with doses of the composition containing a compound of Formula I of the present invention and when appropriate light rays or electromagnetic waves are applied, the compound emits light, i.e. fluorescence. Thereby the existence, position and size of tumor can be detected, i.e., photodiagnosis.

When the tumor is irradiated with light of proper wavelength and intensity, and treated with compound of Formula II of the present invention, the compound is activated to exert a cell killing effect against the tumor. This is called "phototherapy".

Compositions intended for photodiagnosis and phototherapy ideally should have the following properties:

(a) non-toxic at normal therapeutic dosage unless and until activated by light;

(b) should be selectively photoactive;

(c) when light rays or electromagnetic waves are applied, they should emit characteristic and detectable fluorescence;

(d) when irradiated with light rays or electromagnetic waves are applied, they are activated to an extent to exert a cell killing effect against tumor; and (e) easily metabolized or excreted after treatment.

In accordance with testing up to the present, the compounds of the present new therapeutic composition have the foregoing properties and are also characterized by reasonable solubility in water at physiological pH.

The aforesaid compounds of the present composition possess greater fluorescence in tumors than do other tetrapyrroles reported in the prior art. Their use provides the best contrast in tumors compared to normal tissue around the tumor. The instant compounds absorb activating energy for phototherapy in the convenient range of 600 to 800 nanometers, with the preferred compound absorbing in the 620–760 nanometer rang, i.e., light of longer wavelengths which more readily permits penetration of energy into the tumor for phototherapeutic purpose.

In present experience, the present compounds of the present compositions distribute more uniformly throughout the tumor permitting the use of considerably lower dosage which lessens, if not eliminates, photosensitization in the host. They also possess a more consistent fluorescence whereas some of the prior art tetrapyrroles show inconsistent fluorescence or the fluorescence varies from day to day in the host.

The instant composition can be used for diagnosis and therapeutic treatment of a broad range of tumors. Examples of tumors are gastric cancer, enteric cancer, lung cancer, breast cancer, uterine cancer, esophageal cancer, ovarian cancer, pancreatic cancer, pharyngeal cancer, sarcomas, hepatic cancer, cancer of the urinary bladder, cancer of the upper jaw, cancer of the bile duct, cancer of the tongue, cerebral tumor, skin cancer, malignant goiter, prostatic cancer, cancer of the parotid gland, Hodgkins's disease, multiple myeloma, renal cancer, leukemia, and malignant lymphocytoma. For diagnosis, the sole requirement is that the tumor be capable of selectivity fluorescing when exposed to proper light. For treatment, the tumor must be penetrable by the activation energy. For diagnosis, light of shorter wavelength is used whereas for therapeutic purposes light of longer wavelength is used to permit ready penetration of the tumor tissue. Thus, for diagnosis, light of from 360–760 nanometers can be used, and for treatment, from 620–760, depending on the individual characteristics of the tetrapyrrole.

It is necessary that the light rays be so intense as to cause the compounds to emit fluorescence for diagnosis and to exert a cell killing effect for therapy.

The source of irradiation for photodiagnosis and phototherapy is not restricted, however, but the laser beam is preferable because intensive light rays in a desired wavelength range can be selectively applied. For example, in photodiagnosis, the compound of the present composition of the present invention is administered to a human or animal body, and after a certain period of time, light rays are applied to the part to be examined. When an endoscope can be used for the affected part, such as lungs, gullet, stomach, womb, urinary bladder or rectum, it is irradiated using the endoscope, and the tumor portion selectively emits fluorescence. This portion is observed visually, or observed through an adapted fiber scope by eye or on a CRT screen.

In phototherapy, after administration of the dosage, the irradiation is carried out by laser beams from the tip of quartz fibers. Besides the irradiation of the surface of tumor, the internal part of the tumor can be irradiated by inserting the tip of quartz fibers into the tumor. The irradiation can be visually observed or imaged on a CRT screen.

For photodiagnosis, light of wavelengths between 360 and 760 nm. is suitable for activating the present tetrapyrrole compounds. Of course, each compound of the present composition has a specific optimal wavelength of activation. A long wavelength ultra-violet lamp is particularly suitable for photodiagnosis. Similar methods for viewing of the treated tumor can be used as already described for phototherapy.

The dosage of the compounds having the present, new composition will vary depending on the desired effect, whether for diagnosis or for treatment. For diagnosis, doses of as little as 1 mg/kg will be effective, and up to about 20 mg/kg can be used. For treatment, the dose will usually approximate about 0.5 mg/kg. Of course, the dosage for either diagnosis or treatment can be varied widely in view of the advantageous properties of the compounds of the present composition. No mortality of test animals due the present composition has been noted in studies employing dosage levels up to 20 mg/kg.

For both diagnosis and treatment, the compounds of the instant compositions can be administered by the oral, intravenous or intramuscular routes. They can be formulated as lyophilized sterile, pyrogen-free compounds, preferably in the form of basic salts, e.g., sodium salt. The preferred dosage forms are provided as injectable solutions (isotonic).

The irradiation source used in treatment of tumors containing the present composition is a filtered, high-intensity, continuous source or pumped dye, or other laser and light delivery system, which is capable of performing within the following limits: power intensity 20–500 mw/cm$^2$ at wavelengths between 620 and 760 nm. and a total output of at least 500 mw. or greater. Several currently commercial available lasers meet these criteria.

The present tetrapyrroles used in the present composition can be prepared by various synthetic methods which are found in the literature. e.g., Chlorin $e_6$ Willstatter, R. Stoll, A.; *Investigations on Chlorophyll*, (Trans., Schertz, F. M., Merz, A. R.,) p. 176. Science Printing Press, Lancaster, Pa., 1928.

Willstatter, R., Isler, M.; *Ann. Chem.*, 390, 269 (1912).

Fisher, H., Baumler, R.; *Ann Chem.*, 474, 65 (1929).

Fisher, H., Siebel, H.; *Ann. Chem.*, 499, 84 (1932).

Conant, J. B., Mayer, W. W.; *J. Amer. Chem. Soc.*, 52, 3013 (1930).

Fischer and Orth, "Des Chemie des Pyrrole" *Akademische Verlazsgesellschaft, Leipzig*, 1940, Vol. II, Part 2.

General Reference for Porphyrins

"Porphyrins and Metalloporphyrins" ed. Kevin M. Smith, Elsevier 1975 N.Y.

The therapeutic composition of the present invention can be administered to the host in a variety of forms adapted to the chosen route of administration, i.e., orally, intravenously, intramuscularly or subcutaneous routes.

The active compound may be oraly administered, for example, with an inert diluent or with an assimilable edible carrier, or it may be enclosed in hard or soft shell gelatin capsule, or it may be compressed into tablets, or it may be incorporated directly with the food fo the diet. For oral therapeutic administration, the active compound may be incorporated with excipients and used in the form of ingestible tablets, buccal tablets, troches, capsules, elexirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The present new compositions may also be applied directly to tumors, whether internal or external, in the host in topical compositions. Exemplary compositions include solutions of the active compounds in solvents, particularly aqueous solvents, most preferably water. Alternatively, for topical application particularly to skin tumors, the present new compositions may be dispersed in the usual cream or salve formulations commonly used for this purpose or may be provided in the form of spray solutions or suspensions which may include a propellant usually employed in aerosol preparations.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatable with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of tumors in living subjects.

The following examples further illustrate the invention:

In the following examples, photodynamic therapy experiments were carried out in order to determine the efficacy of various chlorin $e_6$ derivatives. These photodynamic therapy experiments have been carried out on DBA/2 Ha Ros-d+Ha mice, using the transplatable tumor, SmT-F. During treatment, the tumors ranged in size between 0.35 and 1.55 cm in diameter.

The general treatment regime is as follows:

DBA/2 Ha Ros-d+Ha mice with SmT-F transplanted tumors in either the exterior part of the hind leg or the side of the mouse were injected intravenously via the external jugular or intraperitoneally with the photosensitizing drug. At the specified time after injection, the area over the tumor was shaved and the light treatment begun.

Light from a Cooper Aurora pumped tunable dye laser was administered via a micro lens system. The optical properties of the lens are such that the light exits the lens in a circular pattern with homogenous intensity throughout the lighted area. The diameter of the lighted area is a function of the distance from the lens.

The light intensity was measured with a Yellow Springs Instrument Model 65A Radiometer at the point of treatment. A 1.5 cm diameter circle of the animal's skin, centered as closely as possible over the tumor, was irradiated in all the experiments. The intensity, wavelength, and dosage of light is included in the data for individual groups of animals. Wavelengths are adjusted, using a Hartridge reversion spectroscope to within 1 nm of the stated value.

Twenty four hours after light treatment, each mouse received 5 mg of Evans Blue Dye intraperitoneally. After an additional two hours, the mice were sacrificed and the tumors were sectioned vertically through the center of the light treated area. Unaffected tumor was stained blue as was unaffected normal tissue. Necrotic or affected areas were white or red in appearance. Measurements on both the whole tumors and affected areas of the tumors were made vertically and horizontally with calipers to the nearest one half millimeter.

The following summary of the experimental results include a range of wavelengths for treatment. This is necessary in order to match the optimal light absorption for each new drug. The conditions described herein result in measurable and significant damage to the tumor.

In all cases except where noted, tissue damage occurred selectively to the tumor tissue as assayed by the Evans Blue method. (See M. C. Berenbaum, *Br. J. Can-* cer, 45; 571 (1982)), even though, in nearly all cases, normal skin overlayed the tumor and the treatment area overlapped significant areas of normal muscle tissue.

The photodynamic therapy is presented in tabular form. Column No. 1 is the dose of chlorin administered to the animal in mg drug per kilogram of mouse body weight. Column No. 2 refers to the time lapse between administration of drug and treatment with laser light. Column No. 3 indicates the type of tumor tested. Column No. 4 indicates the area on the mice on which the tumor was transplanted. Column No. 5 is the intensity of the treatment light in Milliwatts per square centimeter. Column No. 6 is the total light dose administered in terms of Joules per square centimeter. Column No. 7 is the wavelength of the treatment light in nanometers. Column No. 8 measures the average depth of necrosis in the tumor tissue in centimeters, i.e., the distance from the necrotic tip of the tumor next to the skin to the necrotic edge of the tumor most distant from the skin.

S.D. is the standard deviation of the measurement in Column 9.

n is the number of tumors or legs involved in the experiment in Column 10.

Column No. 11 represents the range of depth of necrosis in millimeters within the group.

EXAMPLE I 2-acetyl chlorin $e_6$ was administered in accordance with the foregoing procedure and the results are summarized hereinbelow:

| Drug Dose mg/kg | Time in Hrs. between Drug Introduction & Light Treatment | Tumor Type | Position of Tumor in animal | Light Intensity in mw/cm² | Light Dose in J/cm² | Wavelength used to treat tumors in nm | Depth in cm of effect upon tumor | S.D. | n | range (in cm) |
| --- | --- | --- | --- | --- | --- | --- | --- | --- | --- | --- |
| 100 | 24 | Smt-f | rt. leg | 200 | 300 | 680 | 0.04 ± | 0.08 | 4 | 0.00–0.15 |

The data in the above Table indicates that when the drug is administered under standard conditions and light administered at optimum wavelength after 24 hours, the depth of necrosis extended as far down as 0.15 cm. Moreover, under standard conditions, after 24 hours, the mean depth of necrosis of the tumor cells is 0.04±0.08 cm.

EXAMPLE II 2-formyl chlorin $e_6$ was administered in accordance with the foregoing procedure and the results are tabulated hereinbelow:

| Drug Dose mg/kg | Time in Hrs. between drug introduction and light treatment | Tumor Types | Tumor Position on animal | Light Intensity in mw/cm² | Light Dose in J/cm² | Wavelength used to treat tumors in nm | Mean Depth in cm of effect upon tumor on date of sacrifice | S.D. | n | range |
| --- | --- | --- | --- | --- | --- | --- | --- | --- | --- | --- |
| 100.0 | 24.0 | Smt-f | rt. leg | 200 | 300 | 690 | 0.33 ± | 0.12 | 4 | 0.20–0.45 |

As the data indicates, under standard conditions and light administered at optimum wavelength after 24 hours, the depth of necrosis extended as far down as 0.45 cm; the mean depth of necrosis 24 hours after treatment was 0.33±0.12 cm.

EXAMPLE III

The following table summarizes the tumor effects of deuterochlorin $e_6$ on SmT-F tumors transplanted onto DBA/2 Ha Ros-d+Ha mice according to the foregoing procedure:

| Drug Dose mg/kg | Time in Hrs. between drug introduction and light treatment | Tumor Types | Tumor Position on animal | Light Intensity in mw/cm² | Light Dose in J/cm² | Wavelength used to treat tumors in nm | Mean Depth in cm of effect upon tumor on date of sacrifice | S.D. | n | range |
| --- | --- | --- | --- | --- | --- | --- | --- | --- | --- | --- |
| 100.0 | 24.0 | Smt-f | rt. leg | 200 | 300 | 655 | 0.59 ± | 0.07 | 5 | 0.50–0.70 |

As the data indicates, under standard conditions and light administered at optimum wavelengths after 24 hours, the depth of necrosis extended as far down as 0.70 cm; the mean depth of necrosis 24 hours after treatment was 0.59±0.07 cm.

EXAMPLE IV

The following table summarize the tumor effects of mesochlorin $e_6$ on SmT-F tumors transplanted onto DBA/2 Ha Ros-d+Ha mice, according to the experimental details described hereinabove:

| Drug Dose mg/kg | Time in Hrs. between drug introduction and light treatment | Tumor Types | Tumor Position on animal | Light Intensity in mw/cm² | Light Dose in J/cm² | Wavelength used to treat tumors in nm | Mean Depth in cm of effect upon tumor on date of sacrifice | S.D. | n | range |
| --- | --- | --- | --- | --- | --- | --- | --- | --- | --- | --- |

| | | | | | | | | | | |
|---|---|---|---|---|---|---|---|---|---|---|
| 100.0 | 24.0 | Smt-f | rt. leg | 200 | 300 | 652 | 0.06 ± | 0.08 | 4 | 0.0–0.15 |

As the data indicates, under standard conditions and light administered at optimum wavelengths after 24 hours, the depth of necrosis extended as far down as 0.15 cm; the mean depth of necrosis 24 hours after treatment was 0.06±0.08 cm.

The above preferred embodiments and examples are given to illustrate the scope and spirit of the present invention. These embodiments and examples will make apparent, to those skilled in the art, other embodiments and examples. These other embodiments and examples are within the contemplation of the present invention. Therefore, the present invention should be limited only by the appended claims.

What is claimed is:

1. A pharmaceutical composition for the detection of mammalian tumors which comprises a tumor detecting effective amount of a light-sensitive tetrapyrrole compound of the formula:

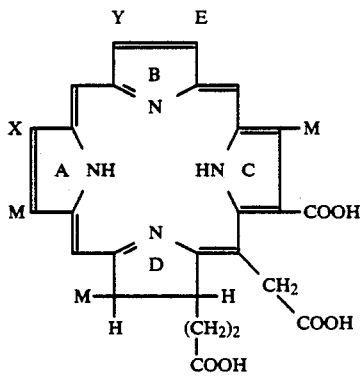

or pharmaceutically acceptable salt thereof wherein

X = H, vinyl, ethyl, acetyl or formyl;

Y = methyl, formyl or $\begin{pmatrix} H \\ methyl \end{pmatrix}$;

M = methyl; and

E = ethyl or $\begin{pmatrix} H \\ ethyl \end{pmatrix}$ and a pharmaceutical carrier therefor, wherein said compound is capable of being activated by light of sufficient wavelength to emit fluorescence thereof.

2. The pharmaceutical composition according to claim 1 wherein
X=H, vinyl, ethyl, acetyl or formyl;
Y=methyl or formyl
M=methyl and;
E=ethyl 3. The pharmaceutical composition according to claim 1 wherein the tetrapyrrole compound is chlorin $e_6$.

4. The pharmaceutical composition according to claim 1 wherein the tetrapyrrole compound is mesochlorin $e_6$.

5. The pharmaceutical composition according to claim 1 wherein the tetrapyrrole compound is bacteriochlorin a.

6. The pharmaceutical composition according to claim 1 wherein the tetrapyrrole compound is 2-desvinylchlorin $e_6$.

7. The pharmaceutical composition according to claim 1 wherein the tetrapyrrole compound is mesochlorin $e_6$.

8. The pharmaceutical composition according to claim 1 wherein the tetrapyrrole compound is 2-acetylchlorin $e_6$.

9. The pharmaceutical composition according to claim 1 wherein the tetrapyrrole compound is 2 formylchlorin $e_6$.

10. The pharmaceutical composition according to claim 1 wherein the tetrapyrrole compound is rhodin $g_7$.

11. A pharmaceutical composition for the treatment of tumors which comprises an anti-tumor effective amount of a light-sensitive tetrapyrrole compound of the formula:

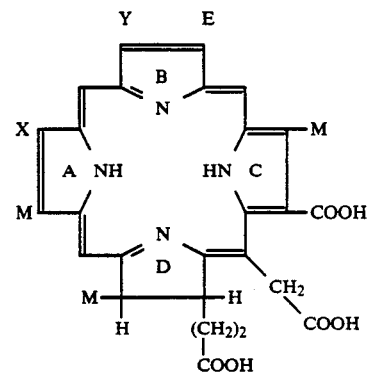

or pharmaceutically acceptable salts thereof wherein

X = H, vinyl, ethyl, acetyl, formyl;

Y = methyl, formyl or $\begin{pmatrix} H \\ methyl \end{pmatrix}$;

M = methyl; and

E = ethyl or $\begin{pmatrix} H \\ ethyl \end{pmatrix}$, and a pharmaceutical carrier therefor, wherein said compound is capable of being activated by light of sufficient wavelength to exert a cell-killing effect on said tumor, with the proviso that said compound is not chlorin $e_6$.

12. The composition of claim 11 wherein
X=H, vinyl, ethyl, acetyl or formyl
Y=methyl or formyl
M=methyl; and
E=ethyl 13. The pharmaceutical composition according to claim 11 wherein the tetrapyrrole compound is mesochlorin $e_6$.

14. The pharmaceutical composition according to claim 11 wherein the tetrapyrrole compound is bacteriochlorin a.

15. The pharmaceutical composition according to claim 11 wherein the tetrapyrrole compound is 2-desvinylchlorin $e_6$.

16. The pharmaceutical composition according to claim 11 wherein the tetrapyrrole compound is 2-acetylchlorin $e_6$.

17. The pharmaceutical composition according to claim 11 wherein the tetrapyrrole compound is 2-formylchlorin $e_6$.

18. The pharmaceutical composition according to claim 11 wherein the tetrapyrrole compound is rhodin $g_7$.

19. A method for the detection tumors in a mammal which comprises administering to said mammal an effective amount of a tetrapyrrole compound according to claim 1; applying light of sufficient wavelength to the area of the mammal to be examined, said wavelength being in the range of about 360 nm to about 760 nm, and observing emitted fluorescence from the tetrapyrrole compound located at said tumor.

20. The method according to claim 19 wherein
X=H, vinyl, ethyl, acetyl or formyl;
Y=methyl or formyl;
M=methyl; and
E=ethyl 21. The method according to claim 19 wherein the tetrapyrrole compound used is chlorin $e_6$.

22. The method according to claim 19 wherein the tetrapyrrole compound is mesochlorin $e_6$.

23. The method according to claim 19 wherein the tetrapyrrole compound used is bacteriochlorin a.

24. The method according to claim 19 wherein the tetrapyrrole compound used is 2-desvinylchlorin.

25. The method according to claim 19 wherein the tetrapyrrole compound used is 2-acetylchlorin $e_6$.

26. The method according to claim 19 wherein the tetrapyrrole compound used is 2-formylchlorin $e_6$.

27. The method according to claim 19 wherein the tetrapyrrole compound used is rhodin $g_7$.

28. A method of treating tumors in mammals which comprises administering to said mammal an effective amount of the tetrapyrrole compound according to claim 11; applying light of sufficient wavelength and intensity to activate said tetrapyrrole compound, said wavelength being in the range from about 600 to about 800 nm, whereby said activated compound exerts a cell-killing effect on said tumor.

29. The method according to claim 28 wherein
X=H, vinyl, ethyl, acetyl or formyl;
Y=methyl or formyl
M=methyl and;
E=ethyl 30. The method according to claim 28 wherein the tetrapyrrole compound used is mesochlorin $e_6$.

31. The method according to claim 28 wherein the tetrapyrrole compound used is bacteriochlorin a.

32. The method according to claim 28 wherein the tetrapyrrole compound used is 2-desvinylchlorin $e_6$.

33. The method according to claim 28 wherein the tetrapyrrole compound used is 2-acetylchlorin $e_6$.

34. The method according to claim 28 wherein the tetrapyrrole compound used is 2-formylchlorin $e_6$.

35. The method according to claim 28 wherein the tetrapyrrole compound used is rhodin $g_7$.

* * * * *

UNITED STATES PATENT AND TRADEMARK OFFICE
CERTIFICATE OF CORRECTION

PATENT NO. : 5,066,274
DATED : November 19, 1991
INVENTOR(S) : Jerry Bommer, et al.

It is certified that error appears in the above-identified patent and that said Letters Patent is hereby corrected as shown below:

Column 2, line 10: delete "M=methyl".

Signed and Sealed this

Fourth Day of May, 1993

Attest:

MICHAEL K. KIRK

Attesting Officer     Acting Commissioner of Patents and Trademarks